(12) United States Patent
Kim et al.

(10) Patent No.: US 8,106,273 B2
(45) Date of Patent: Jan. 31, 2012

(54) TOMATO LINE CHI 128-6025

(75) Inventors: Ilyong Kim, Chungju (KR); Maria Rita Mogno, Latina (IT)

(73) Assignee: Seminis Vegetable Seeds, Inc., Woodland, CA (US)

( * ) Notice: Subject to any disclaimer, the term of this patent is extended or adjusted under 35 U.S.C. 154(b) by 344 days.

(21) Appl. No.: 12/542,560

(22) Filed: Aug. 17, 2009

(65) Prior Publication Data

US 2011/0041206 A1 Feb. 17, 2011

(51) Int. Cl.
*A01H 1/00* (2006.01)
*C07H 21/04* (2006.01)
*C07K 14/415* (2006.01)
*C12N 15/00* (2006.01)

(52) U.S. Cl. ............ 800/317.4; 435/468; 435/411; 435/418; 435/419; 530/370; 536/23.1; 536/23.6; 800/260; 800/278; 800/300; 800/301; 800/302

(58) Field of Classification Search .......... 435/411, 435/468; 530/370; 536/23.6; 800/317.4
See application file for complete search history.

(56) References Cited

U.S. PATENT DOCUMENTS 7,807,885 B2   10/2010  Kim
2009/0119792 A1 *  5/2009  Frantz ................. 800/278
* cited by examiner

*Primary Examiner* — Phuong Bui
(74) *Attorney, Agent, or Firm* — SNR Denton US LLP; Alissa Eagle Esq.

(57) ABSTRACT

The invention provides seed and plants of tomato hybrid HNS12846080 and parent lines thereof. The invention thus relates to the plants, seeds and tissue cultures of such plants, and to methods for producing a tomato plant produced by crossing such plants with themselves or with another tomato plant, including a plant of another genotype. The invention further relates to seeds and plants produced by such crossing. The invention further relates to parts of such plants, including the fruit and gametes of such plants.

24 Claims, No Drawings

US 8,106,273 B2

TOMATO LINE CHI 128-6025

FIELD OF THE INVENTION

The present invention relates to the field of plant breeding and, more specifically, to the development of tomato hybrid HNS12846080 and the inbred tomato lines CHI 128-6025 and CHI 18-2101.

BACKGROUND OF THE INVENTION

The goal of vegetable breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant or plant variety.

Plants that have been self-pollinated and selected for a uniform type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plans, the crossing of these inbred plants, and the evaluation of the crosses. Pedigree breeding and recurrent selection are examples of breeding methods that have been used to develop inbred plants from breeding populations. Those breeding methods combine the genetic backgrounds from two or three or more plants or various other broad-based sources into breeding pools from which new lines are developed by selfing and selection of desired phenotypes. The new lines and hybrids produced therefrom are evaluated to determine which of those have commercial potential.

SUMMARY OF THE INVENTION

In one aspect, the present invention provides a tomato plant of the tomato hybrid designated HNS12846080, tomato line CHI 128-6025, and/or tomato line CHI 18-2101. Also provided are tomato plants having all the physiological and morphological characteristics of such plants. Parts of the tomato plant of the present invention are also provided, for example, including pollen, an ovule, a fruit, a scion, a rootstock and a cell of the plant.

The invention also concerns seed of tomato hybrid HNS12846080, tomato line CHI 128-6025, and/or tomato line CHI 18-2101. The tomato seed of the invention may be provided as an essentially homogeneous population of tomato seed. Essentially homogeneous populations of seeds are generally free from substantial numbers of other seed. Therefore, in one embodiment of the invention seed of tomato hybrid HNS12846080, tomato line CHI 128-6025, and/or tomato line CHI 18-2101 may be defined as forming at least about 97% of the total seed, including at least about 98%, 99% or more of the seed. The population of tomato seed may be particularly defined as being essentially free from hybrid seed. The seed population may be separately grown to provide an essentially homogeneous population of tomato plants.

In another aspect of the invention, a plant of the invention comprising an added heritable trait is provided. The heritable trait may comprise a genetic locus that is, for example, a dominant or recessive allele. In one embodiment of the invention, a plant of the invention is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a plant of the invention is provided. The tissue culture will preferably be capable of regenerating plants capable of expressing all of the physiological and morphological characteristics of the plant from which the tissue is originally obtained, and of regenerating plants having substantially the same genotype as other plants of the starting plant. Examples of some such physiological and morphological characteristics of tomato hybrid HNS12846080, tomato line CHI 128-6025 and tomato line CHI 18-2101 include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides tomato plants regenerated from a tissue culture of the invention, the plants having all the physiological and morphological characteristics of tomato hybrid HNS12846080, tomato line CHI 128-6025 or tomato line CHI 18-2101.

In yet another aspect of the invention, processes are provided for producing tomato seeds, plants and fruit, which processes generally comprise crossing a first parent tomato plant with a second parent tomato plant, wherein at least one of the first or second parent tomato plants is a plant of tomato hybrid HNS12846080, tomato line CHI 128-6025 and/or tomato line CHI 18-2101. These processes may be further exemplified as processes for preparing hybrid tomato seed or plants, wherein a first tomato plant is crossed with a second tomato plant of a different, distinct variety to provide a hybrid that has, as one of its parents, a plant provided herein. In one embodiment of the invention, tomato lines CHI 128-6025 and CHI 18-2101 are crossed to produce hybrid seed of the variety designated HNS12846080. In any cross herein, either parent may be the male or female parent. In these processes, crossing will result in the production of seed. The seed production occurs regardless of whether the seed is collected or not.

In one embodiment of the invention, the first step in "crossing" comprises planting seeds of a first and second parent tomato plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent tomato plants into plants that bear flowers. A third step may comprise preventing self-pollination of the plants, such as by emasculating the male portions of flowers, (i.e., killing or removing the pollen). Self-incompatibility systems may also be used in some hybrid crops for the same purpose. Self-incompatible plants still shed viable pollen and can pollinate plants of other varieties but are incapable of pollinating themselves or other plants of the same variety.

A fourth step for a hybrid cross may comprise cross-pollination between the first and second parent tomato plants. In certain embodiments, pollen may be transferred manually or by the use of insect vectors. Yet another step comprises harvesting the seeds from at least one of the parent tomato plants. The harvested seed can be grown to produce a tomato plant or hybrid tomato plant.

The present invention also provides the tomato seeds and plants produced by a process that comprises crossing a first parent tomato plant with a second parent tomato plant, wherein at least one of the first or second parent tomato plant is tomato hybrid HNS12846080, tomato line CHI 128-6025, and/or tomato line CHI 18-2101. In another embodiment of the invention, tomato seed and plants produced by the process are first filial generation ($F_1$) hybrid tomato seed and plants produced by crossing a plant in accordance with the invention with another, distinct plant. The present invention further contemplates plant parts of such an $F_1$ hybrid tomato plant, and methods of use thereof. Therefore, certain exemplary embodiments of the invention provide an $F_1$ hybrid tomato plant and seed thereof.

In still yet another aspect, the present invention provides a method of producing a plant or a seed derived from one or more of tomato hybrid HNS12846080, tomato line CHI 128-6025, and/or tomato line CHI 18-2101, method comprising the steps of: (a) preparing a progeny plant derived from said variety by crossing a plant of hybrid HNS12846080, tomato line CHI 128-6025 or tomato line CHI 18-2101, with a second plant, wherein said preparing comprises crossing a plant of tomato hybrid HNS12846080, tomato line CHI 128-6025, and/or tomato line CHI 18-2101 with a second plant; and (b) crossing the progeny plant to itself or a second plant to produce a seed of a progeny plant of a subsequent generation.

In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from hybrid HNS12846080, tomato line CHI 128-6025, and/or tomato line CHI 18-2101. The further plant derived from tomato hybrid HNS12846080, tomato line CHI 128-6025, and/or tomato line CHI 18-2101 may be an inbred variety, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant is obtained which possesses some of the desirable traits of the starting plant as well as potentially other selected traits.

The invention also concerns methods of vegetatively propagating a plant of the invention. In certain embodiments, the method comprises the steps of: (a) collecting tissue capable of being propagated from a plant of the invention; (b) cultivating said tissue to obtain proliferated shoots; and (c) rooting said proliferated shoots to obtain rooted plantlets. In some of these embodiments, the method further comprises growing plants from said rooted plantlets.

In another aspect of the invention, a plant of tomato hybrid HNS12846080, tomato line CHI 128-6025, and/or tomato line CHI 18-2101 comprising an added heritable trait is provided. The heritable trait may comprise a genetic locus that is, for example, a dominant or recessive allele. In one embodiment of the invention, a plant of the invention is defined as comprising a single locus conversion. For example, one or more heritable traits may be introgressed at any particular locus using a different allele that confers the new trait or traits of interest. In specific embodiments of the invention, the single locus conversion confers one or more traits such as, for example, herbicide tolerance, insect resistance, disease resistance and modulation of plant metabolism and metabolite profiles. In further embodiments, the trait may be conferred by a naturally occurring gene introduced into the genome of the variety by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

For example, in certain embodiments, the invention provides methods of introducing a desired trait into a plant of the invention comprising: (a) crossing a plant of tomato hybrid HNS12846080, tomato line CHI 128-6025, and/or tomato line CHI 18-2101 with a second tomato plant that comprises a desired trait to produce F1 progeny, (b) selecting an F1 progeny that comprises the desired trait, (c) crossing the selected F1 progeny with a plant of tomato hybrid HNS12846080, tomato line CHI 128-6025, and/or tomato line CHI 18-2101 to produce backcross progeny, and (d) selecting backcross progeny comprising the desired trait and the physiological and morphological characteristic of tomato hybrid HNS12846080, tomato line CHI 128-6025, and/or tomato line CHI 18-2101. The invention also provides tomato plants produced by these methods.

In still yet another aspect of the invention, the genetic complement of tomato hybrid HNS12846080 and tomato lines CHI 128-6025 and CHI 18-2101 is provided. The phrase "genetic complement" is used to refer to the aggregate of nucleotide sequences, the expression of which sequences defines the phenotype of, in the present case, a tomato plant or a cell or tissue of that plant. A genetic complement thus represents the genetic makeup of a cell, tissue or plant, and a hybrid genetic complement represents the genetic make up of a hybrid cell, tissue or plant. The invention thus provides tomato plant cells that have a genetic complement in accordance with the tomato plant cells disclosed herein, and plants and seeds containing such cells.

Plant genetic complements may be assessed by genetic marker profiles, and by the expression of phenotypic traits that are characteristic of the expression of the genetic complement, e.g., gene expression profiles, gene product expression profiles and isozyme typing profiles. It is understood that tomato hybrid HNS12846080, tomato line CHI 128-6025, and/or tomato line CHI 18-2101 could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by tomato plant cells, tissues, plants, and seeds, formed by the combination of a haploid genetic complement of a tomato plant of the invention with a haploid genetic complement of a second tomato plant, preferably, another, distinct tomato plant. In another aspect, the present invention provides a tomato plant regenerated from a tissue culture that comprises a hybrid genetic complement of this invention.

In still yet another aspect, the invention provides a hybrid cherry tomato plant that produces round-shaped fruit, with medium good taste, medium good fruit firmness, and a medium large cherry tomato size; the plant further produces medium long internodes and optimum numbers of flowers per cluster; the plant additionally displays tomato yellow leaf curl virus ("TYLCV") resistance. In certain embodiments, the combination of traits may be defined as controlled by genetic means for the expression of the combination of traits found in tomato hybrid HNS12846080.

In still yet another aspect, the invention provides a method of determining the genotype of tomato hybrid HNS12846080, tomato line CHI 128-6025, and/or tomato line CHI 18-2101 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In certain embodiments, the present invention provides a method of producing tomatoes comprising: (a) obtaining a plant of tomato hybrid HNS12846080, tomato line CHI 128-6025, and/or tomato line CHI 18-2101, wherein the plant has been cultivated to maturity, and (b) collecting tomatoes from the plant.

Any embodiment discussed herein with respect to one aspect of the invention applies to other aspects of the invention as well, unless specifically noted.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, plant parts, seeds and derivatives of tomato hybrid HNS12846080, as well as parent plants capable of being crossed to produce this hybrid, designated tomato line CHI 128-6025 and tomato line CHI 18-2101. These plants show genetic uniformity and stability and horticultural uniformity and stability within the limits of environmental influence for the traits described hereinafter. The plants provide sufficient seed yield. By crossing the parent lines, uniform F1 progeny of hybrid HNS12846080 are obtained.

Hybrid HNS12846080 exhibits a number of improved traits including round-shaped fruit, with medium good taste, medium good fruit firmness, and a medium large cherry tomato size; the plant further produces medium long internodes and optimum numbers of flowers per cluster; the plant additionally displays TYLCV resistance. The development of the hybrid can be summarized as follows. The parents of HNS12846080 are particularly useful for the production of hybrid varieties based on the beneficial traits conferred in hybrid combination.

A. DEVELOPMENT AND CHARACTERISTICS OF TOMATO HYBRID HNS12846080

The tomato hybrid HNS12846080 was produced by a cross of the lines CHI 128-6025 and tomato line CHI 18-2101, generally using CHI 128-6025 as the seed parent. Parent line CHI 128-6025 resulted from an initial cross of lines CHI 128-6005×CHI 128-6022, followed by selfing and selections through the F8 generation. Parent line CHI 18-2101 was developed from an initial cross of FA 139×TySW 4895, followed by selfing and selections through the F7 generation. The crosses and selections that led to the development of tomato hybrid HNS12846080 and its parents are described below:

| Year | Pedigree of female line (CHI 128-6025) | New cherry F1 hybrid (HNS 12846080) | Pedigree of male line (CHI 18-2101) |
|---|---|---|---|
| 1 | | | FA 139 X TySW 4895 |
| 1 | | | F2 |
| 2 | CHI 128-6005 × CHI 128-6022 | | F3 |
| 2 | F2 | | F4 |
| 3 | F3 | | F5 |
| 3 | F4 | | F6 |
| 4 | F5 | F1 combination made | F7 |
| 5 | F6 | Performance trials in research station | |
| 6 | F7 | Performance trials in research station and contract farmer trials | |
| 7 | F8 | Large scale farmer field trials and production | |
| 8 | | Advanced to commercial phase (Phase 2), commercial production | |

In accordance with one aspect of the present invention, there is provided a plant having the physiological and morphological characteristics of tomato hybrid HNS12846080. A description of the physiological and morphological characteristics of tomato hybrid HNS12846080 is presented in Table 1.

TABLE 1

Physiological and Morphological Characteristics of Tomato Hybrid HNS12846080

| CHARACTERISTIC | HNS12846080 |
|---|---|
| 1. Seedling | |
| Anthocyanin in hypocotyl of 2-15 cm seedling | Present (Montfavet H 63.4) |
| Habit of 3-4 week old seedling | Normal |
| 2. Mature plant | |
| Height | 175.3 cm |
| Growth type | Indeterminate (Marmande VR, Saint-Pierre, San Marzano 2) |
| Form | Normal |
| Size of canopy (compared to others of similar type) | Medium |
| Habit | Semi-erect |
| 3. Stem | |
| Anthocyanin coloration of upper third | Absent or very weak |
| Only indeterminate growth type varieties: Stem: length of internode (between 1st and 4th inflorescence) | 62.6 cm Medium (Montfavet 63.5) |
| Branching | Profuse (UC 82) |
| Branching at cotyledon or first leafy node | Present |
| Number of nodes between first inflorescence | 7 to 10 |
| Number of nodes between early (1st to 2nd, 2nd to 3rd) inflorescences | 1 to 4 |
| Number of nodes between later developing inflorescences | 1 to 4 |
| Pubescence on younger stems | Moderately hairy |
| 4. Leaf | |
| Type (mature leaf beneath the 3rd inflorescence) | Tomato |
| Morphology (mature leaf beneath the 3rd inflorescence) | Tomato type leaves deeply divided |
| Margins of major leaflets (mature leaf beneath the 3rd inflorescence) | Shallowly toothed or scalloped |
| Marginal rolling or wiltiness (mature leaf beneath the 3rd inflorescence) | Slight |
| Onset of leaflet rolling (mature leaf beneath the 3rd inflorescence) | Mid season |
| Surface of major leaflets (mature leaf beneath the 3rd inflorescence) | Normal |
| Pubescence (mature leaf beneath the 3rd inflorescence) | Normal |
| Attitude (in middle third of plant) | Semi-drooping (Montfavet H 63.5) |
| Length | 10.5 cm Medium (lorena) |
| Width | 7.2 cm Medium |
| Division of blade | Bipinnate (Lukullus, Saint-Pierre) |
| Size of leaflets (in middle of leaf) | Medium (Marmande VR, Royesta) |
| Intensity of green color | Medium (Lucy) |
| Glossiness (in middle third of plant) | Medium (Marmande VR) |
| Blistering (in middle third of plant) | Medium (Marmande VR) |
| Size of blisters (in middle third of plant) | Medium (Marmande VR) |
| Attitude of petiole of leaflet in relation to main axis (in middle third of plant) | Semi-erect (Blizzard, Marmande VR) |
| 5. Inflorescence | |
| Type (2nd and 3rd truss) | Intermediate (Harzfeuer) |
| Type (observations on the 3rd inflorescence) | Forked (2 major axes) |
| Average number of flowers in inflorescence (observations on the 3rd inflorescence) | 16.7 |
| Leafy or "running" inflorescence (observations on the 3rd inflorescence) | Absent |
| 6. Flower | |
| Calyx | Normal (lobes awl shaped) |
| Calyx-lobes | Approx. equaling corolla |

TABLE 1-continued

Physiological and Morphological Characteristics of Tomato Hybrid HNS12846080

| CHARACTERISTIC | HNS12846080 |
|---|---|
| Corolla color | Yellow |
| Style pubescence | Absent or very scarce (Campbell 1327) |
| Anthers | All fused into tube |
| Fasciation (1st flower of 2nd or 3rd inflorescence) | Absent (Monalbo, Moneymaker) |
| Color | Yellow (Marmande VR) |
| 7. Fruit | |
| Typical shape in longitudinal section (3rd fruit of 2nd or 3rd cluster) | Elliptic |
| Shape of transverse/cross section (3rd fruit of 2nd or 3rd cluster) | Round |
| Shape of stem end (3rd fruit of 2nd or 3rd cluster) | Flat |
| Shape of blossom end (3rd fruit of 2nd or 3rd cluster) | Flat (Montfavet H 63.4, Montfavet H 63.5) |
| Size of blossom scar | Small (Montfavet H 63.4, Montfavet H 63.5) |
| Shape of pistil scar (3rd fruit of 2nd or 3rd cluster) | Dot |
| Peduncle: abscission layer (3rd fruit of 2nd or 3rd cluster) | Present (pedicellate) (Montfavet H 63.5, Roma) |
| Only for varieties with abscission layers: Peduncle: length (from abscission layer to calyx) | 6.9 mm |
| Ribbing at peduncle end | Weak (Early Mech, Hypeel 244, Melody, Peto Gro, Rio Grande) |
| Depression at peduncle end | Absent or very weak (Europeel, Heinz 1706, Rossol, Sweet Baby) |
| Size of stem/peduncle scar | 10.5 mm Very small (Cerise, Heinz 1706, Sweet Baby) |
| Point of detachment of fruit at harvest (3rd fruit of 2nd or 3rd cluster) | At pedicel joint |
| Length of dedicel (3rd fruit of 2nd or 3rd cluster) | 6.9 mm |
| Length of mature fruit (3rd fruit of 2nd or 3rd cluster) | 28.5 mm |
| Diameter of fruit (3rd fruit of 2nd or 3rd cluster) | 28.1 mm |
| Weight of mature fruit (3rd fruit of 2nd or 3rd cluster) | 19.8 grams |
| Size | Mini-tomato |
| Ratio length/diameter | 102% Medium (Early Mech, Peto Gro) |
| Core | Present |
| Size of core in cross section (in relation to total diameter) | 18.4 mm |
| Number of locules | 2 or 3 (Alphamech, Futuria) |
| Surface | Smooth |
| Base color (mature-green stage) | Light gray-green |
| Pattern (mature-green stage) | Green-shouldered |
| Green shoulder (before maturity) | Present (Daniela, Montfavet H 63.5) |
| Shoulder color if different from base | Grey green |
| Extent of green shoulder (before maturity) | Medium (Erlidor, Foxy, Montfavet H 63.5) |
| Intensity of green color of shoulder (before maturity) | Medium (Montfavet H 63.5) |
| Intensity of green color of fruit (before maturity) | Light (Capello, Duranto, Trust) |
| Color at maturity (full-ripe) | Red (Ferline, Daniela, Montfavet H 63.5) |
| Color of flesh at maturity (full-ripe) | Pink (Regina) |
| Flesh color | Uniform |

TABLE 1-continued

Physiological and Morphological Characteristics of Tomato Hybrid HNS12846080

| CHARACTERISTIC | HNS12846080 |
|---|---|
| Locular gel color of table-ripe fruit | Green |
| Firmness | Medium |
|  | (Cristina) |
| Shelf life | Medium |
|  | (Durinta) |
| Time of flowering | Medium |
|  | (Montfavet H 63.5, Prisca) |
| Time of maturity | Medium (Montfavet H 63.5) |
| Ripening | Blossom-to-stem end |
| Ripening | Uniformity |
| Epidermis color | Yellow |
| Epidermis | Normal |
| Epidermis texture | Tough |
| Thickness of pericarp | 3.2 mm |
|  | Thin (Marmande VP) |
| 8. Resistance to fruit disorder | |
| Blossom end rot | Resistant; few symptoms in number and size |
| Blotchy ripening | Highly resistant |
| Bursting | Moderately resistant |
| Catface | Highly resistant |
| Cracking, concentric | Moderately resistant |
| Cracking, radial | Moderately resistant |
| Graywall | Highly resistant |
| Zippering | Highly resistant |
| 9. Disease and pest reaction | |
| Viral diseases | |
| Blotchy ripening | Highly resistant |
| Cracking, concentric | Moderately resistant |
| Tomato yellow leaf curl virus | Present |
|  | (Anastasia, Mohawk, TY 20) |
| Tomato mosaic virus - Strain 0 | Present |
|  | (Mobaci, Mocimor, Moperou) |
| Tomato mosaic virus - Strain 1 | Present |
|  | (Mocimor, Moperou) |
| Tomato mosaic virus - Strain 2 | Present |
|  | (Mobaci, Mocimor) |
| Fungal diseases | |
| *Fusarium* wilt, Race 1 | Highly resistant/ |
| (*F. Oxysporum f. lycopersici*) | present |
|  | (Motelle, Walter) |
| Gray leaf spot | Moderately susceptible |
| (*Stemphylium* spp.) | |
| *Cladosporium fulvum* - Group A | Absent |
|  | (Monalbo) |
| *Cladosporium fulvum* - Group B | Absent |
|  | (Monalbo) |
| *Cladosporium fulvum* - Group C | Absent |
|  | (Monalbo) |
| *Cladosporium fulvum* - Group D | Absent |
|  | (Monalbo) |
| *Cladosporium fulvum* - Group E | Absent |
|  | (Monalbo) |
| *Verticillium dahliae* - Race 0 | Absent |
|  | (Anabel, Marmande verte) |

*These are typical values. Values may vary due to environment. Other values that are substantially equivalent are also within the scope of the invention.

Also provided by the invention are parent lines CHI 128-6025 and CHI 18-2101. A description of these lines follows.

TABLE 2

Physiological and Morphological Characteristics of Tomato Line CHI 128-6025

| CHARACTERISTIC | CHI 128-6025 |
|---|---|
| 1. Seedling | |
| Anthocyanin in hypocotyl of 2-15 cm seedling | Present |
| Habit of 3-4 week old seedling | Normal |

TABLE 2-continued

Physiological and Morphological Characteristics
of Tomato Line CHI 128-6025

| | CHARACTERISTIC | CHI 128-6025 |
|---|---|---|
| 2. | Mature plant | |
| | Height | 150-170 cm |
| | Growth type | Indeterminate (Marmande VR, Saint-Pierre, San Marzano 2) |
| | Form | Normal |
| | Size of canopy (compared to others of similar type) | Medium |
| | Habit | Semi-erect |
| 3. | Stem | |
| | Branching | Profuse (UC 82) |
| | Branching at cotyledon or first leafy node | Present |
| | Number of nodes between first inflorescence | 7 to 10 |
| | Number of nodes between early (1st to 2nd, 2nd to 3rd) inflorescences | 1 to 4 |
| | Number of nodes between later developing inflorescences | 1 to 4 |
| | Pubescence on younger stems | Moderately hairy |
| 4. | Leaf | |
| | Type (mature leaf beneath the 3rd inflorescence) | Tomato |
| | Morphology (mature leaf beneath the 3rd inflorescence) | Tomato type leaves deeply divided |
| | Margins of major leaflets (mature leaf beneath the 3rd inflorescence) | Shallowly toothed or scalloped |
| | Marginal rolling or wiltiness (mature leaf beneath the 3rd inflorescence) | Slight |
| | Onset of leaflet rolling (mature leaf beneath the 3rd inflorescence) | Mid season |
| | Surface of major leaflets (mature leaf beneath the 3rd inflorescence) | Normal |
| | Pubescence (mature leaf beneath the 3rd inflorescence) | Normal |
| 5. | Inflorescence | |
| | Type (make observations on the 3rd inflorescence) | Forked (2 major axes) |
| | Average number of flowers in inflorescence (make observations on the 3rd inflorescence) | 15-20 |
| | Leafy or "running" inflorescence (make observations on the 3rd inflorescence) | Absent |
| 6. | Flower | |
| | Calyx | Normal (lobes awl shaped) |
| | Calyx-lobes | Approx. equaling corolla |
| | Corolla color | Yellow |
| | Style pubescence | Absent or very scarce (Campbell 1327) |
| | Anthers | All fused into tube |
| | Fasciation (1st flower of 2nd or 3rd inflorescence) | Absent (Monalbo, Moneymaker) |
| 7. | Fruit | |
| | Typical shape in longitudinal section (3rd fruit of 2nd or 3rd cluster) | Circular |
| | Shape of transverse/cross section (3rd fruit of 2nd or 3rd cluster) | Round |
| | Shape of stem end (3rd fruit of 2nd or 3rd cluster) | Flat |
| | Shape of blossom end (3rd fruit of 2nd or 3rd cluster) | Flat (Montfavet H 63.4, Montfavet H 63.5) |
| | Shape of pistil scar (3rd fruit of 2nd or 3rd cluster) | Dot |
| | Peduncle: abscission layer (3rd fruit of 2nd or 3rd cluster) | Present (pedicellate) (Montfavet H 63.5, Roma) |
| | Size of stem/peduncle scar | Very small (Cerise, Heinz 1706, Sweet Baby) |
| | Point of detachment of fruit at harvest (3rd fruit of 2nd or 3rd cluster) | At pedicel joint |
| | Length of dedicel (3rd fruit of 2nd or 3rd cluster) | 5-10 mm |
| | Length of mature fruit (3rd fruit of 2nd or 3rd cluster) | 25-30 mm |
| | Diameter of fruit (3rd fruit of 2nd or 3rd cluster) | 25-30 mm |
| | Weight of mature fruit (3rd fruit of 2nd or 3rd cluster) | 18-20 g |
| | Core | Present |
| | Number of locules | 2 or 3 (Alphamech, Futuria) |
| | Surface | Smooth |
| | Base color (mature-green stage) | Light gray-green |
| | Pattern (mature-green stage) | Green-shouldered |
| | Shoulder color if different from base | Grey green |

TABLE 2-continued

Physiological and Morphological Characteristics
of Tomato Line CHI 128-6025

| | CHARACTERISTIC | CHI 128-6025 |
|---|---|---|
| | Color at maturity (full-ripe) | Red (Ferline, Daniela, Montfavet H 63.5) |
| | Color of flesh at maturity (full-ripe) | Pink (Regina) |
| | Flesh color | Uniform |
| | Locular gel color of table-ripe fruit | Green |
| | Ripening | Blossom-to-stem end |
| | Ripening | Uniformity |
| | Epidermis color | Yellow |
| | Epidermis | Normal |
| | Epidermis texture | Average |
| | Thickness of pericarp | Thin (Marmande VR) |
| 8. | Resistance to fruit disorder | |
| | Blossom end rot | Resistant; few symptoms in number and size |
| | Blotchy ripening | Resistant; few symptoms |
| | Bursting | Moderately resistant |
| | Catface | Highly resistant |
| | Cracking, concentric | Moderately resistant |
| | Cracking, radial | Moderately resistant |
| | Graywall | Resistant few symptoms |
| | Zippering | Highly resistant |
| 9. | Disease and pest reaction | |
| | Blotchy ripening | Resistant few symptoms |
| | Cracking, concentric | Moderately resistant |
| | *Fusarium* wilt, Race 1 (*F. Oxysporum f. lycopersici*) | Highly resistant/present (Motelle, Walter) |
| | Gray leaf spot (*Stemphylium* spp.) | Resistant few symptoms |
| 10. | Chemistry and composition of full-ripe fruits | |
| | pH | 4-5 |
| | Soluble solids as °Brix | 6-7 |
| 11. | Phenology | |
| | Fruiting season | Medium (Westover) |
| 12. | Adaptation | |
| | Culture | Greenhouse |
| | Principle use(s): | Home garden |
| | Machine harvest | Not adapted |
| | Regions to which adaptation has been demonstrated | Korea |

*These are typical values. Values may vary due to environment. Other values that are substantially equivalent are also within the scope of the invention.

TABLE 3

Physiological and Morphological Characteristics
of Tomato Line CHI 18-2101

| | CHARACTERISTIC | CHI 18-2101 |
|---|---|---|
| 1. | Seedling | |
| | Anthocyanin in hypocotyl of 2-15 cm seedling | Present (Montfavet H 63.4) |
| | Habit of 3-4 week old seedling | Normal |
| 2. | Mature plant | |
| | Height | 210 cm |
| | Growth type | Indeterminate (Marmande VR, Saint-Pierre, San Marzano 2) |
| | Form | Normal |
| | Size of canopy | Medium |
| | Habit | Semi-erect |
| | Stem: anthocyanin coloration of upper third | Weak (Montfavet H 63.5) |
| | Only indeterminate growth type varieties: Stem: length of internode (between 1st and 4th inflorescence) | Medium (Montfavet H 63.5) |
| 3. | Stem | |
| | Branching | Intermediate (Westover) |
| | Branching at cotyledon or first leafy node | Absent |
| | Number of nodes between first inflorescence | 4 to 7 |
| | Number of nodes between early (1st to 2nd, 2nd to 3rd) inflorescences | 1 to 4 |
| | Number of nodes between later developing inflorescences | 1 to 4 |
| | Pubescence on younger stems | Sparsely hairy (scattered long hairs) |

TABLE 3-continued

Physiological and Morphological Characteristics
of Tomato Line CHI 18-2101

| CHARACTERISTIC | CHI 18-2101 |
|---|---|
| 4. Leaf | |
| Type | Tomato |
| Morphology (mature leaf beneath the 3rd inflorescence) | Tomato type leaves deeply divided |
| Margins of major leaflets (mature leaf beneath the 3rd inflorescence) | Nearly entire |
| Marginal rolling or wiltiness (mature leaf beneath the 3rd inflorescence) | Slight |
| Onset of leaflet rolling (mature leaf beneath the 3rd inflorescence) | Late season |
| Surface of major leaflets (mature leaf beneath the 3rd inflorescence) | Rugose (bumpy or veiny) |
| Pubescence (mature leaf beneath the 3rd inflorescence) | Normal |
| Attitude (in middle third of plant) | Horizontal (Aromata, Triton) |
| Length | Medium (Lorena) |
| Width | Medium |
| Division of blade | Bipinnate (Lukullus, Saint-Pierre) |
| Size of leaflets (in middle of leaf) | Medium (Marmande VR, Royesta) |
| Intensity of green color | Medium (Lucy) |
| Inflorescence: type (2nd and 3rd truss) | Intermediate (Harzfeuer) |
| 5. Inflorescence | |
| Type | Forked (2 major axes) |
| Average number of flowers in inflorescence (make observations on the 3rd inflorescence) | 14 |
| Leafy or "running" inflorescence | Absent |
| 6. Flower | |
| Calyx | Normal (lobes awl shaped) |
| Calyx-lobes | Shorter than corolla |
| Corolla color | Yellow |
| Style pubescence | Sparse |
| Anthers | All fused into tube |
| Fasciation (1st flower of 2nd or 3rd inflorescence) | Absent (Monalbo, Moneymaker) |
| Color | Yellow (Marmande VR) |
| 7. Fruit | |
| Typical shape in longitudinal section (3rd fruit of 2nd or 3rd cluster) | Circular |
| Shape of transverse/cross section (3rd fruit of 2nd or 3rd cluster) | Round |
| Shape of stem end (3rd fruit of 2nd or 3rd cluster) | Flat |
| Shape of blossom end (3rd fruit of 2nd or 3rd cluster) | Indented to flat |
| Shape of pistil scar (3rd fruit of 2nd or 3rd cluster) | Dot |
| Peduncle: abscission layer (3rd fruit of 2nd or 3rd cluster) | Present (pedicellate) (Montfavet H 63.5, Roma) |
| Only for varieties with abscission layers: Peduncle: length (from abscission layer to calyx) | Short (Cerise, Ferline, Montfavet H 63.18, Rossol) |
| Depression at peduncle end | Absent or very weak (Europeel, Heinz 1706, Rossol, Sweet Baby) |
| Size of stem/peduncle scar | Small (Early Mech, Peto Gro, Rio Grande, Roma) |
| Point of detachment of fruit at harvest (3rd fruit of 2nd or 3rd cluster) | At calyx attachment |
| Length of dedicel (3rd fruit of 2nd or 3rd cluster) | 7 mm |
| Length of mature fruit (3rd fruit of 2nd or 3rd cluster) | 26 mm |
| Diameter of fruit (3rd fruit of 2nd or 3rd cluster) | 24 mm |
| Weight of mature fruit (3rd fruit of 2nd or 3rd cluster) | 14 grams |
| Size | Very small (Cerise, Sweet 100) |
| Ratio length/diameter | Medium (Early Mech, Peto Gro) |
| Core | Present |
| Number of locules | Only 2 (Early Mech, Europeel, San Marzano) |
| Surface | smooth |
| Base color (mature-green stage) | Apple or medium green (Heinz 1439 VF) |
| Pattern (mature-green stage) | Radial stripes on sides of fruit |
| Green shoulder (before maturity) | Present (Daniela, Montfavet H 63.5) |
| Shoulder color if different from base | Dark green |

TABLE 3-continued

Physiological and Morphological Characteristics of Tomato Line CHI 18-2101

| CHARACTERISTIC | CHI 18-2101 |
| --- | --- |
| Extent of green shoulder (before maturity?) | Large (Cobra, Delisa, Apona, Manific) |
| Intensity of green color of shoulder (before maturity?) | Dark (Ayala, Erlidor, Xenon) |
| Intensity of green color of fruit (before maturity?) | Medium (Rody) |
| Color at maturity (full-ripe) | Red (Ferline, Daniela, Montfavet H 63.5) |
| Color of flesh at maturity (full-ripe) | Pink (Regina) |
| Flesh color | With lighter and darker areas in walls |
| Locular gel color of table-ripe fruit | Red |
| Firmness | Medium (Cristina) |
| Shelf life | Medium (Durinta) |
| Time of flowering | Medium (Montfavet H 63.5, Prisca) |
| Time of maturity | Medium (Montfavet H 63.5) |
| Ripening | Uniform |
| Ripening | Outside in |
| Epidermis color | Yellow |
| Epidermis | Normal |
| Epidermis texture | Average |
| Thickness of pericarp | Thin (Marmande VR) |
| Dry matter content (at maturity) | Medium |
| 8. Disease and pest reaction | |
| Tomato spotted wilt virus | Highly resistant/present (Lisboa) |
| Tomato yellow leaf curl virus | Present (Anastasia, Mohawk, TY 20) |
| *Cladosporium fulvum* - Group A | Absent (Monalbo) |
| *Cladosporium fulvum* - Group B | Absent (Monalbo) |
| *Cladosporium fulvum* - Group C | Absent (Monalbo) |
| *Cladosporium fulvum* - Group D | Absent (Monalbo) |
| *Cladosporium fulvum* - Group E | Absent (Monalbo) |
| 9. Phenology | |
| Fruiting season | Medium (Westover) |
| Relative maturity in areas tested | Medium |
| 10. Adaptation | |
| Culture | Greenhouse |
| Principle use(s) | Fresh market |
| Machine harvest | Not adapted |
| Regions to which adaptation has been demonstrated | Europe, Middle East and Africa |

*These are typical values. Values may vary due to environment. Other values that are substantially equivalent are also within the scope of the invention.

The parent lines of hybrid HNS12846080 have been self-pollinated and planted for a number of generations to produce the homozygosity and phenotypic stability to make these lines useful in commercial seed production. No variant traits have been observed or are expected for these lines.

The parent lines of hybrid HNS12846080, being substantially homozygous, can be reproduced by planting seeds of the parent lines, growing the resulting tomato plant under self-pollinating or sib-pollinating conditions and harvesting the resulting seeds using techniques familiar to one of skill in the art.

B. EVALUATION OF HYBRID HNS12846080 AND LINES CHI 18-2101 AND CHI 128-6025

As described above, hybrid HNS12846080 exhibits desirable agronomic traits, including producing round-shaped fruit, with medium good taste, medium good fruit firmness, and a medium large cherry tomato size; the plant further produces medium long internodes and optimum numbers of flowers per cluster; the plant additionally displays tomato yellow leaf curl virus ("TYLCV") resistance. These and other performance characteristics of the hybrid were the subject of an objective analysis of the performance traits of the hybrid relative to another hybrid. The results of the analysis are presented below.

TABLE 4

Performance Characteristics For Hybrid HNS12846080

| Trait | HNS 12846080 | Chi Ka (Takii) |
| --- | --- | --- |
| Fruit shape | High round | Round |
| Cracking tolerance | Medium | Medium weak |
| TYLCV resistance | Resistance | Susceptible |
| Fruit taste | Medium good | Good |

As shown above, hybrid HNS12846080 exhibits superior characteristics when compared to competing varieties. An analysis was also carried out on the parents of the hybrid relative to another variety. The results of the analysis are presented below.

TABLE 5

Performance Characteristics For Tomato Line CHI 128-6025

| Trait | CHI 128-6025 | Co Co (Takii) |
| --- | --- | --- |
| Internodes | Medium short | Short |
| Fruit shape | High round | Flattened round |
| Skin shininess | Shiny | A bit dull |

TABLE 5-continued

Performance Characteristics For Tomato Line CHI 128-6025

| Trait | CHI 128-6025 | Co Co (Takii) |
|---|---|---|
| Fruit firmness | Medium firm | Firm |
| Cracking tolerance | Medium strong | Medium |

C. BREEDING OF TOMATO PLANTS

One aspect of the current invention concerns methods for crossing tomato hybrid HNS12846080, tomato line CHI 128-6025, and/or tomato line CHI 18-2101 with itself or a second plant and the seeds and plants produced by such methods. These methods can be used for propagation of hybrid HNS12846080, or can be used to produce hybrid tomato seeds and the plants grown therefrom. Hybrid seeds are produced by crossing tomato hybrid HNS12846080, tomato line CHI 128-6025, and/or tomato line CHI 18-2101 with plants of a different genotype or by selfing hybrid plants.

The development of new varieties using one or more starting varieties is well known in the art. In accordance with the invention, novel varieties may be created by crossing hybrid HNS12846080 followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new line. For development of a uniform variety, often five or more generations of selfing and selection are involved.

Uniform lines of new varieties may also be developed by way of double-haploids. This technique allows the creation of true breeding lines without the need for multiple generations of selfing and selection. In this manner, true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant provided herein and progeny thereof to achieve a homozygous line.

Backcrossing can also be used to improve an inbred plant. Backcrossing transfers one or more desirable traits from one inbred or non-inbred source to an inbred that lacks those traits. This can be accomplished, for example, by first crossing a superior inbred (A, recurrent parent) to a donor inbred (non-recurrent parent), which carries the appropriate locus or loci for the trait in question. The progeny of this cross are then mated back to the superior recurrent parent (A), followed by selection in the resultant progeny for the desired trait to be transferred from the non-recurrent parent. After five or more backcross generations with selection for the desired trait, the progeny have characteristic being transferred, but are like the superior parent for most or almost all other loci. The last backcross generation would be selfed to give pure breeding progeny for the trait being transferred.

The parental tomato plant which contributes the desired characteristic or characteristics is termed the non-recurrent parent because it can be used one time in the backcross protocol and therefore need not recur. The parental tomato plant to which the locus or loci from the non-recurrent parent are transferred is known as the recurrent parent as it is used for several rounds in the backcrossing protocol.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection or screening may be applied where the single locus (e.g. allele) acts in a dominant fashion. For example, when selecting for a dominant allele providing resistance to a bacterial disease, the progeny of the initial cross can be inoculated with bacteria prior to the backcrossing. The inoculation then eliminates those plants which do not have the resistance, and only those plants which have the resistance allele are used in the subsequent backcross. This process is then repeated for all additional backcross generations.

Although backcrossing methods are simplified when the characteristic being transferred is a dominant allele, recessive, co-dominant and quantitative alleles may also be transferred. In this instance, it may be necessary to introduce a test of the progeny to determine if the desired locus has been successfully transferred. In the case where the non-recurrent parent was not homozygous, the F1 progeny would not be equivalent. F1 plants having the desired genotype at the locus of interest could be phenotypically selected if the corresponding trait was phenotypically detectable in a heterozygous or hemizygous state. In the case where a recessive allele is to be transferred and the corresponding trait is not phenotypically detectable in the heterozygous of hemizygous state, the resultant progeny can be selfed, or crossed back to the donor to create a segregating population for selection purposes. Non-phenotypic tests may also be employed. Selected progeny from the segregating population can then be crossed to the recurrent parent to make the first backcross generation (BC1).

Molecular markers may also be used to aid in the identification of the plants containing both a desired trait and having recovered a high percentage of the recurrent parent's genetic complement. Selection of tomato plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay that is able to identify the relative presence or absence of a trait of interest in a plant can also be useful for breeding purposes. Procedures for marker assisted selection applicable to the breeding of tomato are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Simple Sequence Repeats (SSR), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

Tomato hybrids and lines can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Tomatoes are grown for use as rootstocks or scions. Typically, different types of tomatoes are grafted to enhance disease resistance, which is usually conferred by the rootstock, while retaining the horticultural qualities usually conferred by the scion. It is not uncommon for grafting to occur between *Solanum lycopersicum* varieties and related *Solanum* species. Methods of grafting and vegetative propagation are well-known in the art.

Tomato hybrid HNS12846080, tomato line CHI 128-6025, and/or tomato line CHI 18-2101 are particularly well suited for the development of new hybrids or lines based on the elite nature of their genetic backgrounds. In selecting a second plant to cross with tomato hybrid HNS12846080, tomato line CHI 128-6025, and/or tomato line CHI 18-2101 for the purpose of developing novel tomato hybrids or lines, it will typically be preferred to choose those plants that either themselves exhibit one or more selected desirable characteristics or that exhibit the desired characteristic(s) when in hybrid combination. Examples of desirable characteristics may include, but are not limited to herbicide tolerance, pathogen resistance (e.g., insect resistance, nematode resistance, resistance to bacterial, fungal, and viral disease), male fertility, improved harvest characteristics, enhanced nutritional quality, increased antioxidant content, improved processing characteristics, high yield, improved characteristics related to the fruit flavor, texture, size, shape, durability, shelf life, and yield, improved vine habit, increased soluble solids content, uniform ripening, delayed or early ripening, reduced blossom end scar size, seedling vigor, adaptability for soil conditions, and adaptability for climate conditions. Qualities that may be desirable in a processing tomato are not necessarily those that would be desirable in a fresh market tomato; thus, the selection process for desirable traits for each specific end use may be different. For example, certain features, such as solids content, and firm fruit to facilitate mechanical harvesting are more desirable in the development of processing tomatoes; whereas, external features such as intensity and uniformity of fruit color, unblemished fruit, and uniform fruit size are typically more important to the development of a fresh market product that will have greater retailer or consumer appeal. Of course, certain traits, such as disease and pest resistance, high yield, and concentrated fruit set are of interest in any type of tomato variety.

D. PLANTS OF THE INVENTION DERIVED BY GENETIC ENGINEERING

Many useful traits that can be introduced by backcrossing, as well as directly into a plant, are those that are introduced by genetic transformation techniques. Genetic transformation may therefore be used to insert a selected transgene into tomato hybrid HNS12846080, tomato line CHI 128-6025, and/or tomato line CHI 18-2101 or may, alternatively, be used for the preparation of tomato hybrids or lines containing transgenes that can be subsequently transferred to tomato hybrid HNS12846080, tomato line CHI 128-6025, and/or tomato line CHI 18-2101 by crossing. Methods for the transformation of plants, including tomato, are well known to those of skill in the art. Techniques which may be employed for the genetic transformation of tomato include, but are not limited to, electroporation, microprojectile bombardment, *Agrobacterium*-mediated transformation, pollen-mediated transformation, and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

To effect pollen-mediated transformation, one may apply pollen pretreated with DNA to the female reproductive parts of tomato plants for pollination. A pollen-mediated method for the transformation of tomato is disclosed in U.S. Pat. No. 6,806,399.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target tomato cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant species where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for tomato plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly, partially duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wunl, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the tomato varieties of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a tomato plant according to the invention. Non-limiting examples of particular genes and corresponding phenotypes one may choose to introduce into a tomato plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (e.g., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

E. DEFINITIONS

In the description and tables herein, a number of terms are used. In order to provide a clear and consistent understanding of the specification and claims, the following definitions are provided:

Alleles: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

F₁ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Locus: A designated location on a chromosome.

Marker: A readily detectable phenotype, preferably inherited in codominant fashion (both alleles at a locus in a diploid heterozygote are readily detectable), with no environmental variance component, i.e., a heritability of 1.

Polyploid: A cell or organism containing three or more complete sets of chromosomes.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits whose phenotypes are usually continuously distributed.

Regeneration: The development of a plant from tissue culture.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Self-pollination: The transfer of pollen from the anther to the stigma of the same plant.

Single Locus Converted (Conversion) Plant: Plants, which are developed by a plant breeding technique called backcrossing, wherein essentially all of the desired morphological and physiological characteristics of a tomato line are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a tomato plant by transformation.

Triploid: A cell or organism having three sets of chromosomes.

F. DEPOSIT INFORMATION

A deposit of tomato hybrid HNS12846080, tomato line CHI 128-6025, and tomato line CHI 18-2101, disclosed above and recited in the claims, will be made with the American Type Culture Collection (ATCC), 10801 University Blvd., Manassas, Va. 20110-2209. The dates of deposit are Nov. 4, 2008, Nov. 10, 2008 and Oct. 29, 2008, respectively. The accession numbers for those deposited seeds are ATCC Accession No. PTA-9564, ATCC Accession No. PTA-9567, and ATCC Accession No. PTA-9542, respectively. Upon issuance of a patent, all restrictions upon the deposits will be removed, and the deposits are intended to meet all of the requirements of 37 C.F.R. §1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
U.S. Pat. No. 5,378,619
U.S. Pat. No. 6,806,399
WO 99/31248
An et al., *Plant Physiol.*, 88:547, 1988.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997
Gull et al., *J. Amer. Soc. Hort. Sci.* 114:950-954, 1989.
Kader et al. *Hort. Sci.*, 13:577-578, 1978.
Klee et al., *Bio-Technology*, 3(7):637-642, 1985.
Kopecky et al., Crop Science, 45:274-281, 2005.
Kuhlemeier et al., *Plant Cell*, 1:471, 1989.
Linstrom, *Genetics*, 26:387-397, 1940.
Marcotte et al., *Nature*, 335:454, 1988.
Marcotte et al., *Plant Cell*, 1:969, 1989.
Odel et al., *Nature*, 313:810, 1985.
Omirulleh et al., *Plant Mol. Biol.*, 21(3):415-428, 1993.
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 18:6531-6535, 1990.

What is claimed is:

1. A tomato plant comprising at least a first set of the chromosomes of tomato line CHI 128-6025, a sample of seed of said line having been deposited under ATCC Accession Number PTA-9567.

2. A seed comprising at least a first set of the chromosomes of tomato line CHI 128-6025, a sample of seed of said line having been deposited under ATCC Accession Number PTA-9567.

3. The plant of claim 1, which is inbred.

4. The plant of claim 1, which is hybrid.

5. The seed of claim 2, wherein the seed produces an inbred plant of line CHI 128-6025.

6. A plant part of the plant of claim 1.

7. The plant part of claim 6, further defined as a leaf, an ovule, pollen, a fruit, or a cell.

8. A tomato plant, or a part thereof, having all the physiological and morphological characteristics of the tomato plant of claim 3.

9. A tissue culture of regenerable cells of the plant of claim 1.

10. The tissue culture according to claim 9, comprising cells or protoplasts from a plant part selected from the group consisting of embryos, meristems, cotyledons, pollen, leaves, anthers, roots, root tips, pistil, flower, seed and stalks.

11. A tomato plant regenerated from the tissue culture of claim 10.

12. A method of vegetatively propagating the plant of claim 1 comprising the steps of:
    (a) collecting tissue capable of being propagated from the plant according to claim 1;
    (b) cultivating said tissue to obtain proliferated shoots; and
    (c) rooting said proliferated shoots to obtain rooted plantlets.

13. The method of claim 12, further comprising growing plants from said rooted plantlets.

14. A method of introducing a desired trait into a tomato line comprising:
    (a) crossing a plant of line CHI 128-6025, a sample of seed of said line having been deposited under ATCC Accession Number PTA-9567, with a second tomato plant that comprises a desired trait to produce F1 progeny;
    (b) selecting an F1 progeny that comprises the desired trait;
    (c) crossing the selected F1 progeny with a plant of line CHI 128-6025 to produce backcross progeny;
    (d) selecting backcross progeny comprising the desired trait and the physiological and morphological characteristics of tomato line CHI 128-6025; and
    (e) repeating steps (c) and (d) three or more times in succession to produce selected fourth or higher backcross progeny that comprises the desired trait.

15. A tomato plant produced by the method of claim 14.

16. A method of producing a plant comprising an added desired trait, the method comprising introducing a transgene conferring the desired trait into a plant of tomato line CHI 128-6025, a sample of seed of said line having been deposited under ATCC Accession Number PTA-9567.

17. A method of determining the genotype of the plant of claim 1 comprising obtaining a sample of nucleic acids from said plant and detecting in said nucleic acids a plurality of polymorphisms, thereby determining the genotype of the plant.

18. The method of claim 17, further comprising the step of storing the results of detecting the plurality of polymorphisms on a computer readable medium.

19. A method for producing a seed of a plant derived from tomato line CHI 128-6025 comprising the steps of:
    (a) crossing a tomato plant of tomato line CHI 128-6025, a sample of seed of said line having been deposited under ATCC Accession Number PTA-9567 with a second tomato plant; and
    (b) allowing seed of a tomato line CHI 128-6025-derived tomato plant to form.

20. The method of claim 19, further comprising the steps of:
    (c) crossing a plant grown from said tomato line CHI 128-6025-derived tomato seed with itself or a second tomato plant to yield additional tomato line CHI 128-6025-derived tomato seed;
    (d) growing said additional tomato line CHI 128-6025-derived tomato seed of step (c) to yield additional tomato line CHI 128-6025-derived tomato plants; and
    (e) repeating the crossing and growing steps of (c) and (d) to generate at least a first further tomato line CHI 128-6025-derived tomato plant.

21. The method of claim 19, wherein the second tomato plant is of an inbred tomato line.

22. The method of claim 20, further comprising:
    (f) crossing the further tomato line CHI 128-6025-derived tomato plant with a different tomato plant to produce seed of a hybrid progeny plant.

23. A method of producing a tomato fruit comprising:
    (a) obtaining the plant according to claim 1, wherein the plant has been cultivated to maturity; and
    (b) collecting tomato from the plant.

24. A method of producing tomato seed comprising crossing the plant of claim 1 with itself or a second tomato plant and allowing seed to form.

* * * * *